United States Patent [19]

Donati et al.

[11] Patent Number: 5,206,262
[45] Date of Patent: Apr. 27, 1993

[54] SOLUBLE SALTS OF IBUPROFEN AND NAPROXEN WITH N-(2-HYDROXYETHYL) PYRROLIDINE AND PHARMACEUTIC COMPOSITIONS CONTAINING SAID SALTS

[75] Inventors: Elisabetta Donati, Breccia, Italy; Irina Rapaport, Rovio, Switzerland; Paolo Lualdi, Grandate, Italy

[73] Assignee: Altergon S.A., Lugano, Switzerland

[21] Appl. No.: 902,824

[22] Filed: Jun. 23, 1992

[30] Foreign Application Priority Data

Jul. 1, 1991 [IT] Italy ............... 001804 A/91

[51] Int. Cl.$^5$ .............. A61K 31/40; C07D 207/06
[52] U.S. Cl. ................... 514/428; 548/474; 562/466; 562/496
[58] Field of Search ............ 548/574; 514/428; 562/466, 496

[56] References Cited

U.S. PATENT DOCUMENTS

| | | | |
|---|---|---|---|
| 3,637,767 | 1/1972 | Alvarez | 562/466 |
| 4,948,805 | 8/1990 | Ziggiotti et al. | 514/428 |
| 4,994,604 | 2/1991 | Tung et al. | 562/496 |
| 5,019,563 | 5/1991 | Hunter et al. | 536/103 |
| 5,028,625 | 7/1991 | Motola et al. | 514/557 |

Primary Examiner—Joseph Paul Brust
Assistant Examiner—Mary Susan H. Gabilan
Attorney, Agent, or Firm—Stevens, Davis, Miller & Mosher

[57] ABSTRACT

The salts, in the crystalline form, of ibuprofen and naproxen with N-(2-hydroxyethyl) pyrrolidine are prepared by dissolving ibuprofen and naproxen respectively in a suitable organic solvent, by adding N-(2-hydroxyethyl) pyrrolidine, by letting the compounds react, by removing the solvent and by crystallizing the obtained salt from a solution in an apolar and aprotic solvent.

Said salts have a high solubility in water and are used for preparing pharmaceutic compositions for oral and other administrations.

8 Claims, No Drawings

SOLUBLE SALTS OF IBUPROFEN AND NAPROXEN WITH N-(2-HYDROXYETHYL) PYRROLIDINE AND PHARMACEUTIC COMPOSITIONS CONTAINING SAID SALTS

PRIOR ART

Ibuprofen (2-(4-isobutylphenyl)-propionic acid) and naproxen (6-methoxy-α-methyl-2-naphthalen acetic acid) are anti-inflammatory drugs (NSAID) which have been known for a long time and are described, for instance, in British patent 971,700 and in U.S. Pat. No. 3,637,767 respectively.

The drawback of the salts with inorganic cations of aforesaid drugs is a low solubility in water.

On the other hand, salts of diclofenac with cyclic organic bases are known, which salts are suitable for preparing aqueous pharmaceutic compositions and are obtained by crystallization from hexane or ligroine, as described in U.S. Pat. No. 4,948,805. These salts crystallize easily from hexane and ligroine as well as from other solvents such as acetone and ethanol.

However, up to now it was not possible to obtain ibuprofen and naproxen salts with cyclic organic bases in the form of crystalline solids, as no suitable solvent for the crystallization had been found.

In fact it was noted that the ibuprofen and naproxen salts with the same cyclic organic bases, contrary to the diclofenac salts, do not crystallize from aforesaid solvents, even after several weeks of cooling at −20° and that, by evaporation of the solvent, said salts are often in the form of oils.

SUMMARY

The problem of obtaining ibuprofen and naproxen salts with N-(2-hydroxyethyl)pyrrolidine, in the crystalline form, has been now solved by dissolving ibuprofen or naproxen in a suitable organic solvent, to which freshly distilled N-(2-hydroxyethyl) pyrrolidine is then added, by letting said compounds react, by removing the solvent and by crystallizing the obtained salt, from solutions in apolar and aprotic solvents. Ibuprofen and naproxen salts with N-(2-hydroxyethyl)pyrrolidine in the crystallized form are thus obtained, which have a high solubility in water and are suitable for preparing pharmaceutic compositions both in the liquid form (aqueous solutions) and in the solid form.

DETAILED DESCRIPTION OF THE INVENTION

The present invention relates to crystalline salts of ibuprofen (2-(4-isobutylphenyl)-propionic acid) and of naproxen (6-methoxy-α-methyl-2-naphthalen acetic acid) with N-(2-hydroxyethyl) pyrrolidine, to a process for preparing said salts and to pharmaceutic compositions containing same such as, for instance, monodose granular compositions, soft gelatin capsules, topical creams and gels, collyria, vaginal lavages, plasters and the like. A particular advantage of said salts consists in that these salts, when they are prepared in the granular form and kept in monodose light-proof and water-proof envelopes, contrary to the form in tablets used at present for oral administration of ibuprofen and naproxen, allow to prepare extemporaneous aqueous solutions, characterized by a very low gastoinjury, while keeping completely the activity level.

Moreover the salts of the invention present the advantage of having no disagreable taste and can therefore be used, without any problem, for oral administration.

Therefore the salts, in the crystalline form, of ibuprofen and naproxen with N-(2-hydroxyethyl) pyrrolidine are an object of the present invention and the pharmaceutic compositions containing active therapeutic doses of said salts are a further object of the invention.

The process for the preparation of these salts consists in dissolving ibuprofen and naproxen respectively in a suitable organic solvent, in adding N-(2-hydroxyethyl)-pyrrolidine, in letting said compounds react, in separating the raw product by cooling, followed by solvent filtration or distillation, and in crystallizing the product obtained from a suitable apolar or aprotic solvent.

Organic solvents suitable for dissolving ibuprofen and naproxen as well as for letting the reaction take place are the following: ethanol, methanol, acetone, diethyl ether, dichloromethane, chloroform, carbon tetrachloride, diisopropyl ether.

Hydroxyethyl pyrrolidine, used for the reaction, must be distilled freshly and is employed in an equimolecular amount or in an amount slightly in excess with respect to ibuprofen and naproxen.

The synthesis process concerning the raw product to be obtained, is characterized by the following conditions: concentration of the reaction product in the reaction mixture ranging from 10% to 70% by weight, reaction temperature ranging from 20° to 30° C. over a period of time ranging from 0.1 to 2 hours, with or without stirring, cooling temperature for the separation of the raw product ranging from −10° to −40° C. over a period of time ranging from 10 to 30 hours.

The raw product, both in the crystalline and in the oily form, is purified by crystallization under the following conditions: aprotic, apolar and anhydrous solvent, preferably diethyl ether, ethyl acetate, diisopropyl ether, dichloromethane, chloroform, carbon tetrachloride or mixtures of said solvents, concentration ranging from 10% to 70% by weight, temperature ranging from −10° to −40° C., period of time ranging from 10 to 30 hours.

The final products are then obtained by the customary processes of filtration, drying and so on.

Ibuprofen/N-(2-hydroxyethyl)pyrrolidine salt, has a melting point ranging from 52° to 55° C. and molecular weight 321.4; Naproxen/N-(2-hydroxyethyl)pyrrolidine salt has a melting point ranging from 70° to 72° C. and molecular weight 345.4.

The aforesaid salts are hygroscopic, crystalline, white solids, having a fresh, neutral taste and no particular smell.

Owing to their hygroscopicity, they tend to absorb the environment humidity, if they are not kept in air tight containers, given rise to highly concentrated solutions with the characteristic smell of the base.

The naproxen and ibuprofen/N-(2-hydroxyethyl)-pyrrolidine salts, on the contrary, are characterized by a good stability, when they are sheltered from light and humidity.

The stability proves to be satisfactory also in both solid and liquid pharmaceutic forms.

The solubility characteristics of the ibuprofen (IH) and naproxen (NH) salts with N-(2 hydroxyethyl)pyrrolidine, compared with the respective sodium salts (INa) and (NNa), are set forth in the following table:

| Compound | Solubility (% w/v) | pH of the solution (1% w/w) |
| --- | --- | --- |
| IH | >50% | 6.75 |
| NH | >50% | 6.70 |
| INa | <5% | 7.53 |
| NNa | <15% | 7.63 |

The pharmaceutic compositions according to the present invention, which are useful in the anti-inflammatory therapy, contain a therapeutically active amount of ibuprofen or naproxen salt with N-(2-hydroxyethyl)pyrrolidine and liquid or solid excipients, of the organic or inorganic type, for pharmaceutic use, suitable for preparing formulations for oral, parenteral or topic use.

The following examples are reported with an illustrating, but not limiting purpose of the present invention.

EXAMPLE 1

Preparation of naproxen salt with N-(2-hydroxyethyl)pyrrolidine 10 g (0.0434 moles) of naproxen were dissolved in ethanol (15 ml) and 5.1 g (0.0442 moles) of freshly distilled N-(2-hydroxyethyl)pyrrolidine were added to the thus obtained solution. The mixture was kept under stirring for 1 hour at room temperature and after addition of 150 ml of ethylether, was put into a freezer at $-20°$ C. for 24 hours.

The obtained raw product, after having been separated by filtration and cold-dried under vacuum, presented a melting temperature equal to $55°-60°$ C. This product, after having been dissolved again in the same amount of weight of anhydrous diethyl ether, was crystallized at a temperature of $-20°$ C. for 24 hours. 12 g of a crystalline salt (yield 80%) were obtained which have a melting temperature of $70°-72°$ C.

EXAMPLE 2

Preparation of ibuprofen salt with N-(2-hydroxyethyl) pyrrolidine 10 g of ibuprofen (0.0485 moles) were dissolved in 10 g of anhydrous diethyl ether; 5.60 g (0.0486 moles) of freshly distilled N-(2-hydroxythyl)pyrrolidine were added to the solution. The solution was stirred at room temperature for 1 hour, afterwards it was put into a freezer at $-20°$ C. for 24 hours. The raw product was separated by filtration and cold-dried under vacuum: melting point 48° C. The product was dissolved at room temperature in the same amount by weight of anhydrous diethyl ether. The solution was cooled at $-20°$ C. for 24 hours. 13 g of a crystalline salt (yield 83%) were obtained which have a melting point of $52°-55°$ C.

EXAMPLE 3

10 g of ibuprofen (0.0485 moles) were dissolved in 15 g of anhydrous ethyl acetate; 5.60 g (0.0486 moles) of freshly distilled N-(2-hydroxyethyl)pyrrolidine were added to the solution. The solution was stirred at room temperature for 1 hour till complete dissolution of the reactants, afterwards it was put into a freezer at $-20°$ C., in the presence of a seed consisting of salt crystals previously obtained. After 4 hours the salt precipitation began; the solution was kept in the freezer for 24 hours. The raw product was separated by filtration and cold-dried under vacuum: melting point $48°-50°$ C. The raw product was crystallized by dissolving it at room temperature in the same amount by weight of anhydrous ethyl acetate and by cooling the solution in the freezer at $-20°$ C. for 24 hours. 13 g of crystalline salt (yield 80%) were obtained, which have a melting point of $52°-55°$ C.

EXAMPLE 4

Granular compositions in monodose envelopes, to be dissolved in water before being taken

|  | mg per dose |
| --- | --- |
| Ibuprofen/N-(2-hydroxyethyl)pyrrolidine salt or | from 312 to 936 |
| Naproxen/N-(2-hydroxyethyl)pyrrolidine salt | from 375 to 750 |
| Edulcorating substances (Saccharin, Aspartame, Acesulfame) | from 10 to 80 |
| Optional binders (Sorbitol, PVP) | from 5 to 20 |
| Flavours (Fruit taste, Mint, Liquorice, and the like) | from 100 to 200 |
| Optional anti-adhering agents (precipitated colloidal silica) | from 1 to 5 |
| Acariogenic sugars (Sorbitol, Xylitol, Maltitol, and the like) in an amount sufficient to reach | 2000 or 3000 |

The granular compositions were prepared by wet way, by a fluid bed or by dry way by compression and subsequent grinding. The aromatic fraction could be added by mixing.

We claim:

1. Soluble salt, in the crystalline form, of a non-steroid anti-inflammatory drug (NSAID) selected from the group consisting of ibuprofen (2-(4-isobutylphenyl)-proprionic acid) and naproxen (6-methoxy-α-methyl-2-naphthalenacetic acid) with N-(2-hydroxyethyl)pyrrolidine.

2. A process for preparing soluble salts, in the crystalline form, of non-steroid anti-inflammatory drugs (NSAID) selected from the group consisting of ibuprofen(2-(4-isobutylphenylpropionic acid) and naproxen (6-methoxy-α-methyl-2-naphthalenacetic acid) with N-(2-hydroxyethyl)pyrrolidine wherein:
   a. Naproxen or Ibuprofen are dissolved in a suitable organic solvent and N-(2-hydroxyethyl)pyrrolidine is added to the solution:
   b. the mixture is let react at a temperature ranging from 20° to 30° C.;
   c. the raw product is separated by cooling at a temperature ranging from $-10°$ to $-40°$ C., followed by solvent filtration or evaporation;
   d. the obtained raw product is dissolved again in an aprotic, apolar and anhydrous solvent and crystallized at a temperature ranging from $-10°$ to $-40°$ C.

3. A process, according to claim 2, wherein said organic solvent for the dissolution of Naproxen or Ibuprofen is selected from the group consisting of ethanol, methanol, acetone, diethyl ether, dichloromethane, chloroform, carbon tetrachloride, diisopropyl ether.

4. A process, according to claim 2, wherein said N-(2-hydroxyethyl)pyrrolidine is used in an equimolecular amount or in an amount slightly in excess with respect to Ibuprofen or Naproxen.

5. A process, according to claim 2, wherein said reaction is carried out in such a way as to have in the reaction mixture a concentration of the reaction product ranging from 10% to 70% by weight.

6. A process, according to claim 2, wherein said solvent for the crystallization is selected from the group consisting of diethyl ether, ethyl acetate, diisopropyl ether, dichloromethane, chloroform, carbon tetrachloride and mixtures of said solvents.

7. A process, according to claim 2, wherein said crystallization is carried out with a salt concentration ranging from 10% to 70% by weight.

8. Pharmaceutic compositions, useful in the anti-inflammatory therapy, containing therapeutically active amounts of a soluble in the crystalline form, salt consisting of a non-steroid anti-inflammatory drug (NSAID) selected from the group consisting of ibuprofen and naproxen with N-(2-hydroxyethyl)pyrrolidine together with pharmaceutic excipients suitable for oral, parenteral and topic administration.

* * * * *